(12) United States Patent
Heil et al.

(10) Patent No.: US 8,393,817 B2
(45) Date of Patent: Mar. 12, 2013

(54) SMALL ELECTRICAL APPLIANCE (75) Inventors: Benedikt Heil, Ober-Moerlen (DE);
Hansjoerg Reick, Cincinnati, OH (US);
Michael Stolper, Eschborn (DE);
Andreas Kramp, Bad Camberg (DE);
Norbert Schaefer, Frankfurt/Main (DE)

(73) Assignee: Braun GmbH, Kronberg (DE)

( * ) Notice: Subject to any disclaimer, the term of this patent is extended or adjusted under 35 U.S.C. 154(b) by 440 days.

(21) Appl. No.: 12/599,504

(22) PCT Filed: May 26, 2008

(86) PCT No.: PCT/EP2008/004163
§ 371 (c)(1),
(2), (4) Date: Jul. 13, 2010

(87) PCT Pub. No.: WO2008/145321
PCT Pub. Date: Dec. 4, 2008

(65) Prior Publication Data
US 2010/0284728 A1 Nov. 11, 2010

(30) Foreign Application Priority Data

May 30, 2007 (DE) .......................... 10 2007 025 385
Dec. 29, 2007 (DE) .......................... 10 2007 063 150

(51) Int. Cl.
*A46B 11/02* (2006.01)
*B43K 5/02* (2006.01)
(52) U.S. Cl. ..................... 401/188 R; 401/282; 15/167.1
(58) Field of Classification Search .............. 401/188 R, 401/282, 283, 284, 269; 15/22.2, 110, 167.1–167.3; 433/80, 82, 89
See application file for complete search history.

(56) References Cited

U.S. PATENT DOCUMENTS

| | | | | |
|---|---|---|---|---|
| 4,060,870 A | * | 12/1977 | Cannarella | 15/24 |
| 5,142,723 A | * | 9/1992 | Lustig et al. | 15/22.1 |
| 6,164,967 A | | 12/2000 | Sale et al. | |
| 6,902,337 B1 | * | 6/2005 | Kuo | 401/188 R |
| 6,957,925 B1 | | 10/2005 | Jacobs et al. | |
| 7,080,980 B2 | * | 7/2006 | Klupt | 433/80 |
| 7,469,440 B2 | * | 12/2008 | Boland et al. | 15/22.1 |
| 7,972,136 B2 | * | 7/2011 | Hegemann | 433/80 |
| 7,993,067 B2 | * | 8/2011 | Hall et al. | 401/188 R |
| 2005/0271531 A1 | | 12/2005 | Brown et al. | |

FOREIGN PATENT DOCUMENTS

| | | |
|---|---|---|
| DE | 20 19 003 A1 | 11/1971 |
| DE | 199 35 067 A1 | 2/2001 |
| DE | 10 2005 045226 A1 | 3/2007 |
| JP | 2006 061486 | 3/2006 |
| WO | WO 03/101365 A | 12/2003 |

OTHER PUBLICATIONS

PCT International Search Report dated Sep. 23, 2008.

* cited by examiner

*Primary Examiner* — David Walczak
*Assistant Examiner* — Jennifer C Chiang
(74) *Attorney, Agent, or Firm* — John P. Colbert

(57) ABSTRACT

An electric toothbrush is disclosed. The tootbrush includes two elements to be driven, wherein the first element is a movable brush head and the second element is a pump; an electric motor; and a device that drives the movable brush head in both directions of rotation of the electric motor and drives the pump in one direction of rotation.

10 Claims, 8 Drawing Sheets

SMALL ELECTRICAL APPLIANCE

The invention relates to a small electrical appliance, for example an electric toothbrush, with two elements to be driven and an electric motor.

An electric toothbrush with two elements to be driven is known for example from U.S. Pat. No. 6,957,925 B1. This electric toothbrush has a separate drive unit for each element to be driven, namely a brush head and a pump to convey toothpaste from a reservoir into the brush head.

It is the object of the invention to specify a small electrical appliance that has a compact design and is inexpensive to produce.

To achieve this object, a small electrical appliance according to the invention has a device that drives the first and/or the second element depending on the direction of rotation of the electric motor.

If the small electrical appliance is an electric toothbrush, the first element to be driven can be a movable brush head, and the second element to be driven can be a pump, for example for conveying a care agent from a reservoir via a channel into the brush head. In this case it is advantageous if the device drives the brush head at both directions of rotation of the electric motor, but drives the pump only at one direction of the electric motor. It is thereby assumed that it is irrelevant with regard to the cleaning effect whether the brush head is driven in the one or the other direction of rotation, or whether a reversal of direction of rotation takes place during cleaning. Consequently, in this case the change in direction of rotation only affects a switching on and off of the pump. There can, however, also be two pumps present, of which only the first is driven by the one direction of rotation of the electric motor, and only the second, or the first and the second pump, is driven by the other direction of rotation of the electric motor.

Another embodiment of an electric toothbrush has a first and a second reservoir for two different dental care agents. In this toothbrush, a first electric motor is thus present to drive the brush head and a second electric motor is present to drive the two pumps, wherein the first and/or the second pump is driven according to the direction of rotation of the second electric motor. Because the first and/or the second pump can alternatively be driven by the second electric motor by means of a device, depending on the direction of rotation of the second electric motor, two different dental care agents can be conveyed one after the other or simultaneously via the corresponding channels from the reservoirs to a brush head. In order to improve oral hygiene, it is advantageous to convey different dental care agents into the brush head, for example:

A: A first dental care agent cleans the plaque from teeth, after which a second dental care agent is conveyed with a high fluoride content for caries prophylaxis.

B: A first dental care agent cleans the teeth; the teeth are subsequently polished with a second dental care agent having fine abrasive ingredients.

C: A first dental care agent cleans the plaque from teeth; after which a second dental care agent is applied with brighteners to whiten the teeth.

D: Two different care agents, which can only be stored separately because otherwise they would immediately react with one another, are simultaneously conveyed so that they only react with one another in the brush head.

The invention is described in more detail by the following exemplary embodiments.

Figure 1:
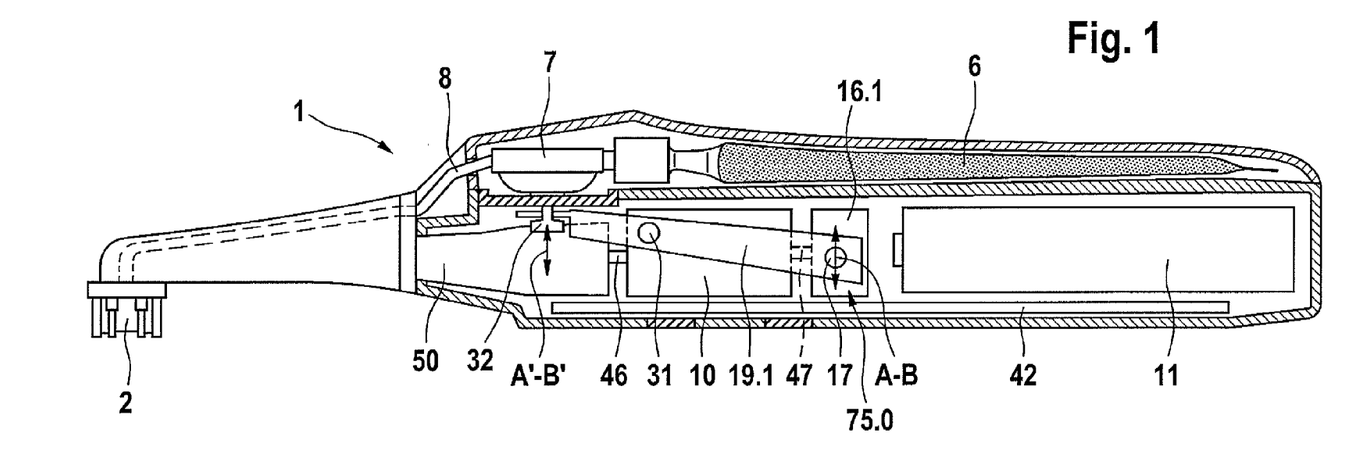
FIG. 1 shows a cross section side view of an electric toothbrush with a brush head in a first exemplary embodiment.

FIG. 1 shows in a cross section side view an electric toothbrush 1 with a brush head 2, with two elements to be driven and with an electric motor 10 in a first exemplary embodiment of a small electrical appliance. The first element to be driven is a movable brush head 2 and the second element to be driven is a pump 7, preferably a diaphragm valve pump, wherein the electric motor 10 in its first and second directions of rotation drives the first element (brush head 2) and in its second direction of rotation drives the second element (pump 7).

The brush head 2 is constantly driven (if necessary via a gear 50) independently of the first and the second direction of rotation by a first shaft journal 46, wherein a device 16.1 is connected to a second shaft journal 47 of the electric motor 10 by means of the pump 7 which can additionally be driven at the second direction of rotation. The device 16.1 has a single overrunning clutch 75.0, which drives the pump 7 in the coupling function. Thereby, the brush head 2 is driven in both (first and second) directions of rotation and the pump 7 is additionally driven in the second direction of rotation.

In the coupling function, the simple overrunning clutch 75.0 transfers the output movements A-B by means of an output shaft 17, which, via an actuating lever 19.1, a joint 31, and an element 32, activates the pump 7 by means of the transferred output movements A'-B' to apply a care agent to the brush head 2, wherein the electric toothbrush 1 is provided with a reservoir 6 for the care agent, which reservoir is connected via the pump 7 to a channel 8 which discharges into the brush head 2. A disposable or rechargeable battery 11 serves as the power supply for the electric motor 10.

Figure 2:
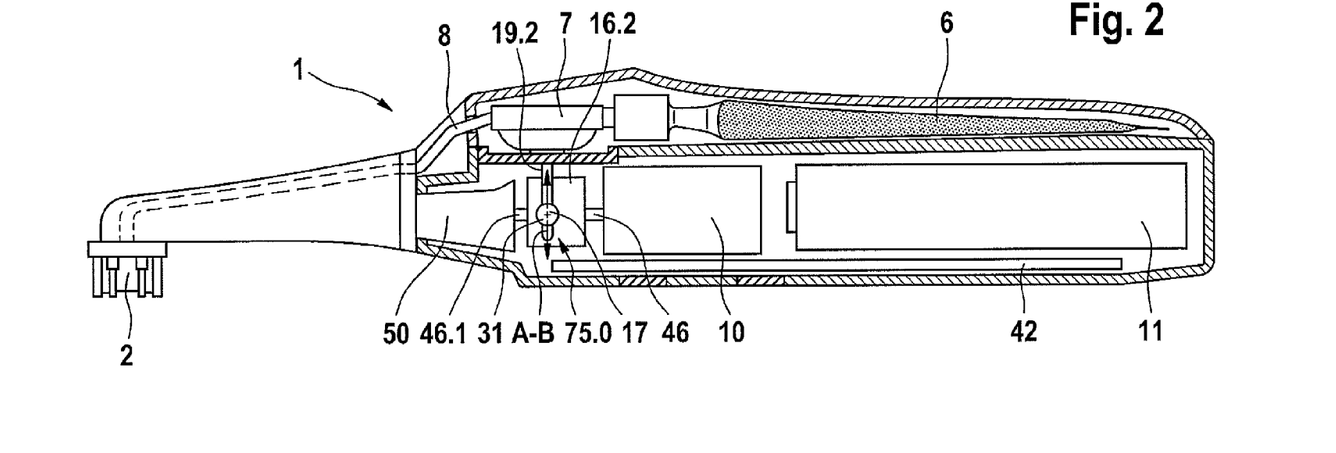
FIG. 2 shows a cross section side view of an electric toothbrush with a brush head in a second exemplary embodiment.

FIG. 2 shows in a cross section side view an electric toothbrush 1 with a brush head 2, with two elements to be driven and with an electric motor 10 in a second exemplary embodiment of a small electrical appliance. The first element to be driven is a movable brush head 2 and the second element to be driven is a pump 7, preferably a diaphragm valve pump, wherein the electric motor 10 in its first and second directions of rotation drives the first element (brush head 2) and in its second direction of rotation drives the second element (pump 7).

The brush head 2 is constantly driven (if necessary via a gear 50) independently of the first and the second directions of rotation by a one-sided shaft journal 46 of the electric motor 10, wherein the shaft journal 46 of the electric motor 10 is connected to a device 16.2 by means of the pump 7 which can additionally be driven at the second direction of rotation. The shaft journal 46 as the drive train extends through the device 16.2 as the extension 46.1 to the brush head gear 50. The device 16.2 has a single overrunning clutch 75.0 that drives the pump 7 in the coupling function via an actuating lever 19.2. Thereby, the brush head 2 is driven in both (first and second) directions of rotation (for example by oscillating rotating movements) and the pump 7 is additionally driven in the second direction of rotation.

In the coupling function, the simple overrunning clutch 75.0 transfers the output movements A-B by means of an output shaft 17, which, via an actuating lever 19.2 with a joint 31, activates the pump 7 to apply a care agent to the brush head 2, wherein the electric toothbrush 1 is provided with a reservoir 6 for the care agent, which reservoir is connected via the pump 7 to a channel 8 which discharges into the brush head 2. A disposable or rechargeable battery 11 serves as the power supply for the electric motor 10.

Figure 3:
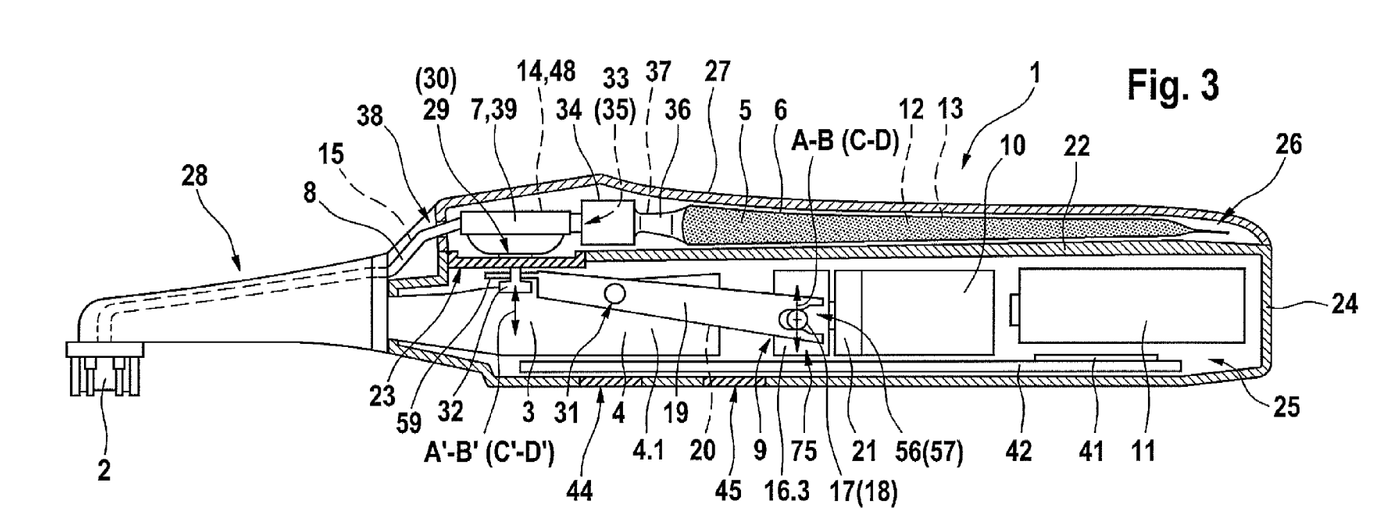
FIG. 3 shows a cross section side view of an electric toothbrush with a brush head in a third exemplary embodiment.

FIG. 3 shows in a cross section side view an electric toothbrush 1 with a brush head 2, which can be driven by a second drive unit 3 with a second electric motor 4. A first reservoir 6 is provided for a first liquid dental care agent 5, which reservoir is connected via the pump 7 to a channel 8 which discharges into the brush head 2. The first pump 7 can be driven by a first electric motor 10 of a first drive unit 9, wherein the first and the second electric motors 10, 4 are supplied with power by a disposable or rechargeable battery 11.

A second reservoir 13 is provided for a second liquid dental care agent 12, which reservoir is connected via a second pump 14 to a second channel 15 which discharges into the brush head 2. The first or the second pump 7, 14 can alternatively be driven by the electric motor 10 by means of a device 16.3, depending on the direction of rotation of the first electric motor 10. Because the device 16.3, by means of a double overrunning clutch 75.1, converts a first direction of rotation of the shaft of the first electric motor 10 via a gear 21 into output movements A-B of a first output shaft 17 and a second (opposite) direction of rotation into output movements C-D of a second output shaft 18 (thus driving either the first or the second output shaft 17, 18), a further electric motor and also a further gear for the second output shaft become superfluous, which results not only in a more compact and lighter weight design of the electric toothbrush 1, but also reduced production costs.

The electric toothbrush 1 has a removable brush attachment 28 with a coupling connection to convey the two dental care agents 5, 12.

The first and the second output shafts 17, 18 of the device 16.3 are laterally arranged on two opposing sides, wherein the first output shaft 17 transfers output movements A-B at a first direction of rotation of the first electric motor 10 and the second output shaft 18 transfers output movements C-D at a second (opposite) direction of rotation of the first electric motor 10. The first output shaft 17 corresponds with a first actuating lever 19 and the second output shaft 18 corresponds with a second, adjacently arranged actuating lever 20, which levers according to the lever rule transfer via a pivot joint 31 in each case, corresponding output movements A'-B' or C'-D' to the first pump 7 (or the first diaphragm pump 39) and to the second pump 14 (or second diaphragm pump 48), by which means a corresponding pump activation takes place and results in conveying the first and the second dental care agents 5, 12.

Thereby, an optimum simplification of assembly is reached in that the device 16.3 forms a component 49 (FIG. 5) with the first electric motor 10, with the gear 21, and with the first and second actuating levers 19, 20.

A first or second diaphragm valve pump 39, 48 is provided as the first and second pump 7, 14, which diaphragm valve pump is activated by external output movements A'-B', C'-D' of the first or second actuating lever 19, 20, and elastically returns to its shape.

In addition, the arrangement of the first and the second drive units 9, 3 and the disposable or rechargeable battery 11 in a line results in a compact and slender design and good handling of the electric toothbrush 1.

A first and a second chamber 25, 26 are formed in the (hard plastic) housing 24 of the electric toothbrush 1 by a liquid-tight partition 22 with an integrated soft membrane 23. The second chamber 26 is provided externally with a resealable cover 27 (FIGS. 3 and 4), which enables an easy exchange of the empty reservoirs 6, 13 with filled reservoirs 6, 13. The first and the second drive units 9, 13 and the disposable or rechargeable battery 11 are arranged in a line in the first chamber 25. The first and the second adjacently arranged reservoirs 6, 13 as well as the first and the second pumps 7, 14 are arranged in the second chamber 25.

A transmission of the movements from the first and the second actuating levers 19, 20 takes place through contact with the elastic soft membrane 23 on the first and the second adjacently arranged pumps 7, 14, which are each in contact at an actuating zone 29, 30 with the soft membrane 23 in each case. Thereby, the first and the second diaphragm valve pumps 39, 48 are activated by corresponding movements of the elastic soft membrane 23, and thus a liquid-tight barrier is created between the first and the second chambers 25, 26, by which means a possible contamination by a liquid (for example the first or second dental care agent 5, 12 or rinse water) from the second chamber 26 into the first chamber 25 is effectively prevented.

The sequence of movements from the first output shaft 17 of the device 16.3 to the diaphragm valve pump 39 is carried out such that, at a first direction of rotation of the shaft of the first electric motor 10, linear output movements A-B to the first output shaft 17 result. The output movements A-B are transmitted from a beginning of the first actuating lever 19—preferably made from a dimensionally rigid sheet metal part—via a joint 31 and by means of a plastic element 32 at one end of the first actuating lever 19 across the elastic soft membrane 23 to the actuating zone 29 of the first diaphragm valve pump 39 and is thus activated. At a second (opposite) direction of rotation of the shaft, only the second output shaft 18 of the device 16.3 is displaced in linear output movements C-D and correspondingly only the second diaphragm valve pump 48 is activated. If a practically simultaneous application of the first and second dental care agents 5, 12 is necessary, this is achieved by a periodic, short switching of the directions of rotation of the shaft of the first electric motor 10, wherein the respective application amount (volume flow rate) can be controlled by a programmable control device 41 using the ratio of the respective duration and the respective direction of rotation. For this purpose, the first electric motor 10 is connected to the programmable control device 41, by which means the direction of rotation and the circuit times and thereby the dosage amounts (volume flow rate) of the first and the second dental care agents 5, 12 into the brush head 2 can be specified. The control device 41 is located in the first chamber 25 on an electronic circuit board 42 which is located close to an inner side 43 of the first chamber 25, so that a switch (not shown) on the electronic circuit board 42 can be activated via flexible housing wall zones 44, 45 which enable a liquid-tight activation of the switch.

A respective first and second inlet 33, 35 of the first and second pumps 39, 48 is connected to a coupling piece 34 to connect a first and second container neck 36, 37 of the replaceable first and second reservoir 6, 13.

Figure 4:
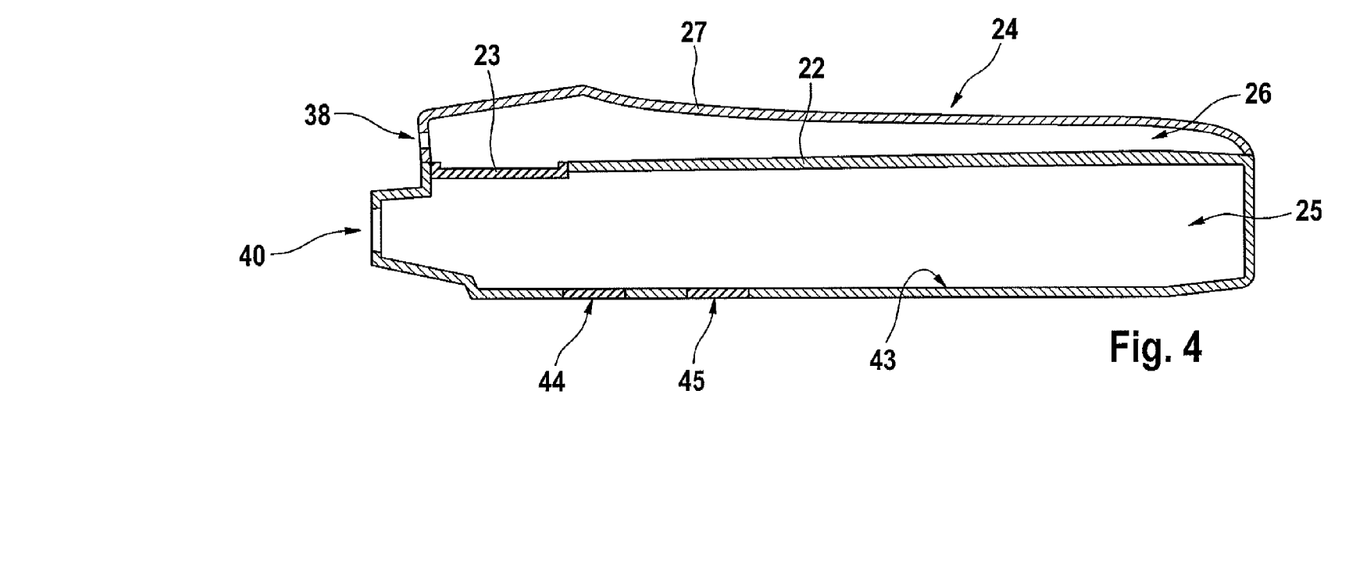
FIG. 4 shows a cross section side view of only a housing for the electric toothbrush according to FIG. 3.

FIG. 4 shows in a cross section side view only a housing 24 of the electric toothbrush 1 according to FIG. 3, wherein the housing 24, by means of the liquid-tight partition 22 having an integrated soft membrane 23, forms a first and a second chamber 25, 26. The second chamber 26 is accessible from the outside by opening a hinged back cover part 27. A first opening 38 serves as a passage for the first channel 8, to which the first diaphragm valve pump 39 is connected. A second opening 40 serves as a passage for the second (first) drive unit 3. Corresponding flexible housing wall zones 44, 45 are provided for manual activation of electric switches (not shown).

Figure 5:
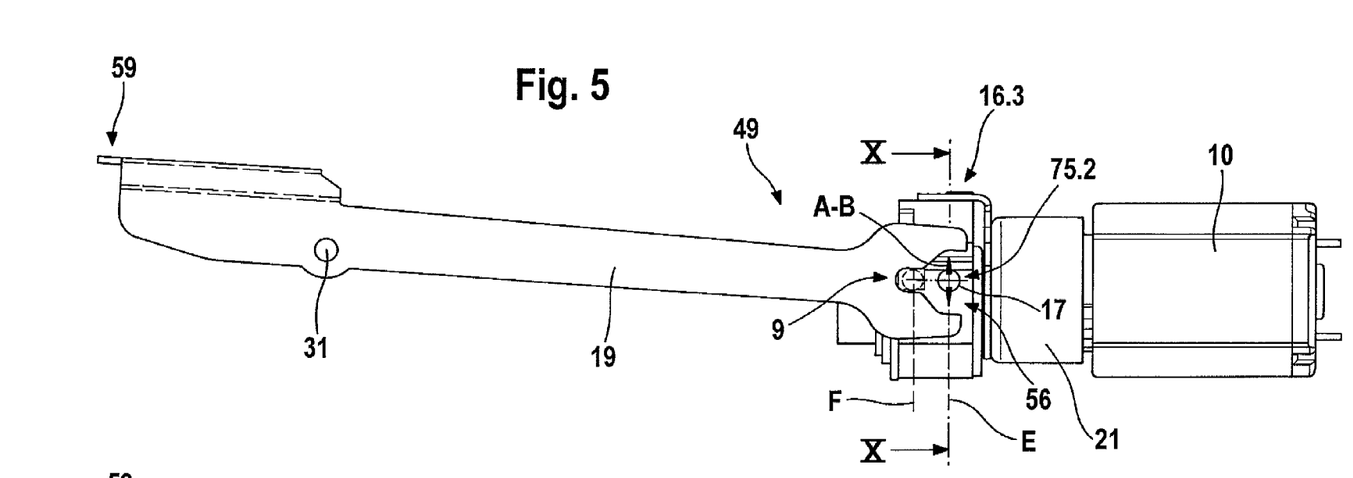
FIG. 5 shows a freestanding side of a section from FIG. 3 with a device having a double overrunning clutch in the form of an eccentric coupling.
Figures 9, 10:
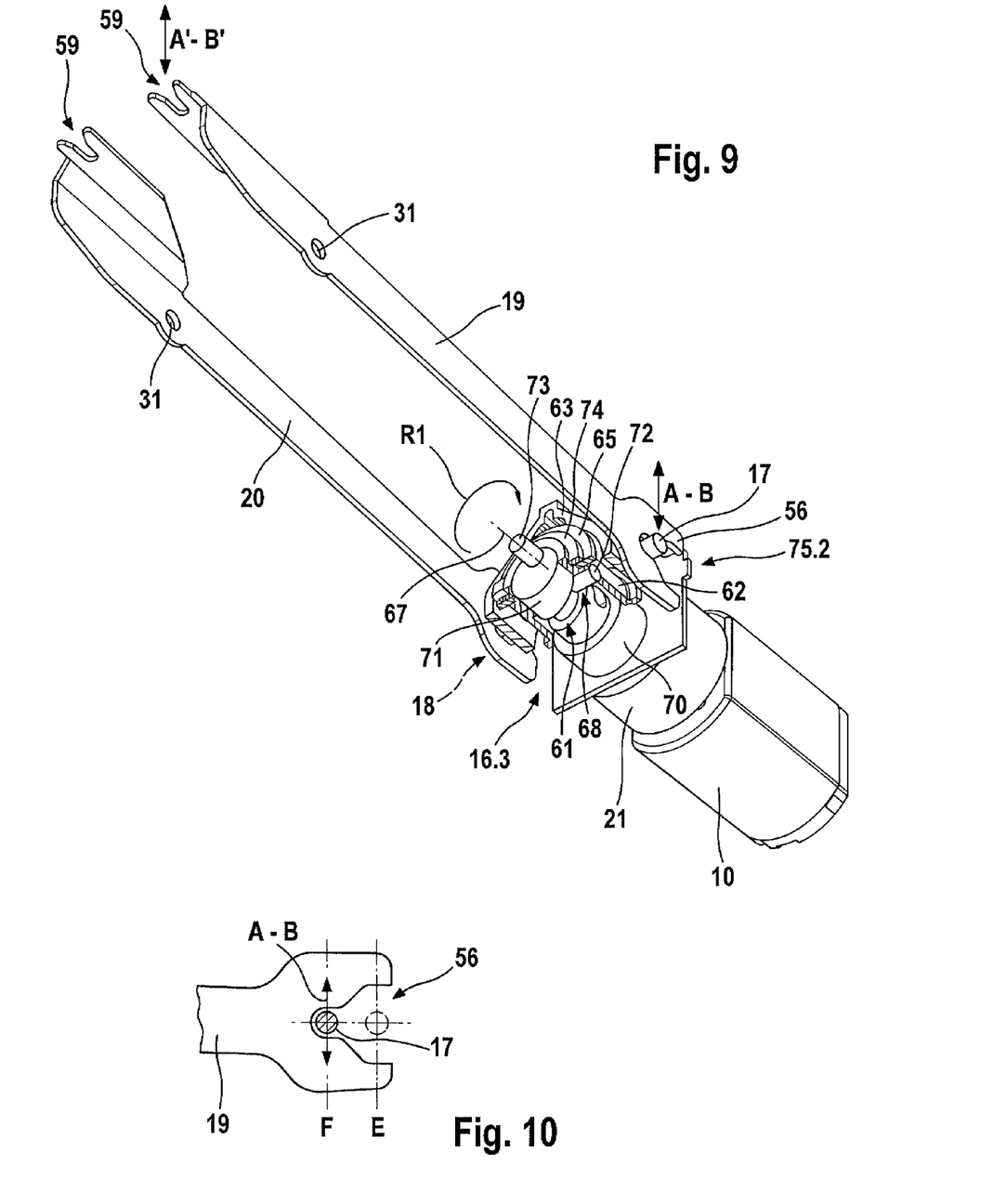
FIG. 9 shows a perspective side view of the device with the drive unit for two pumps according to FIG. 5, however in a position "F", wherein a casing and a valve are not shown.
FIG. 10 shows a detailed representation of the first driving fork according to FIG. 9.

FIG. 5 shows the device 16.3 with the double overrunning clutch 75 and with the first drive unit 9 for the first and the second pumps 7, 14 (FIG. 3). The first actuating lever 19 has a first driving fork 56 on its free end which corresponds with the output shaft 17. On the other free end of the actuating lever 19, a connecting element 59 is located for mounting the plastic element 32 (FIG. 3), wherein the corresponding output movements A'-B' are transferred to the connecting element 59 and the plastic element 32 via the joint 31. Because the output shaft 17 in position E (FIG. 10) idles or encounters no resistance due to the width of the first driving fork 56, no output movements A-B are transmitted to the actuating lever 19 and thus the first pump 7 is also not activated. If on the other hand, the output shaft 17 is in the position F, the output shaft 17 is engaged by the constriction of the first driving fork 56 and transmits output movements A'-B' (FIG. 9).

Figure 6:
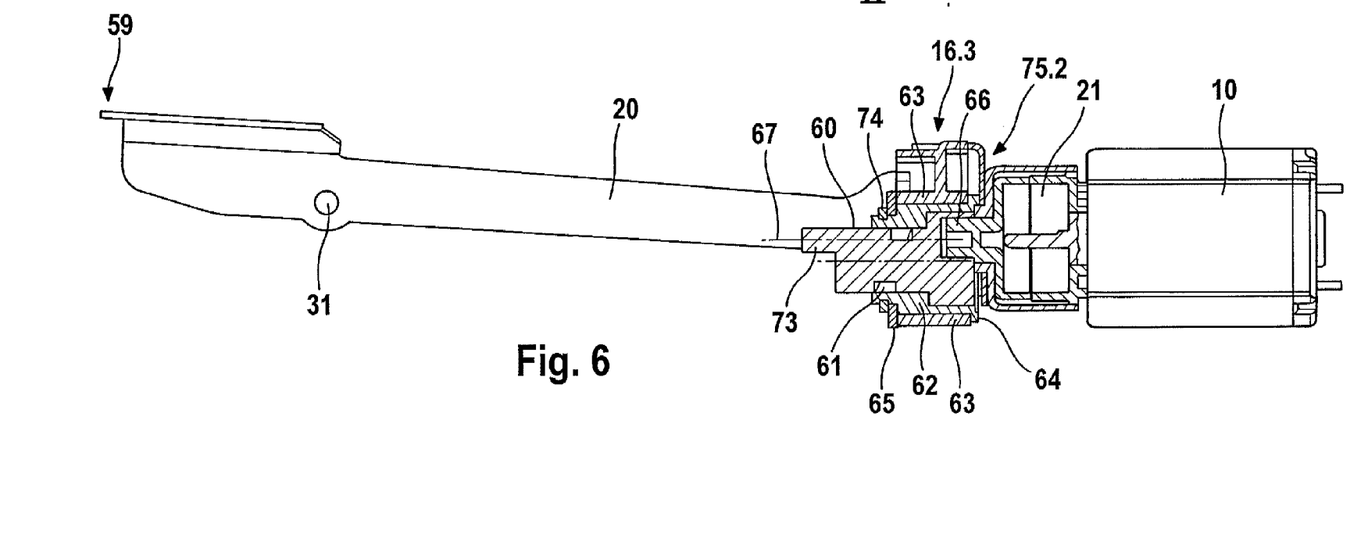
FIG. 6 shows a cross section side view of a section from FIG. 3 corresponding to FIG. 5.

In a cross section side view, FIG. 6 shows the device 16.3 with an eccentric coupling 75.2 and with a first drive unit 9 for the two pumps 7, 14 according to FIG. 5, however, with a second actuating lever 20. The eccentric coupling has an eccentric body 60 with a helical groove 61 (FIG. 7), a casing 62, an oval valve 63, a bearing collar 64, a disc 65, a shaft journal 73, and a locking ring 74.

Figure 7:
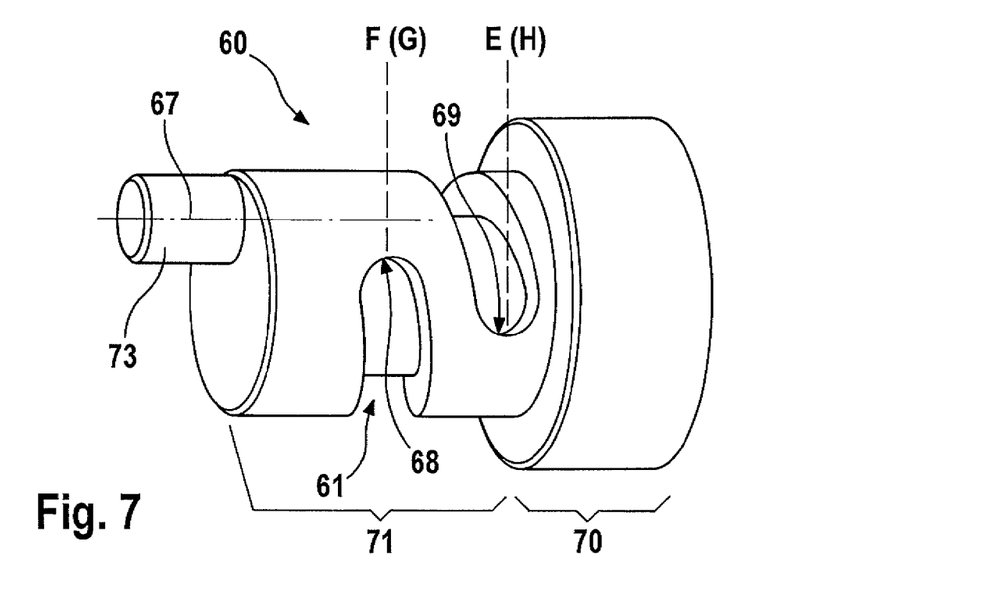
FIG. 7 shows a perspective side view of an eccentric body with a helical groove.

The elongated eccentric body 60 is arranged axially fixed on the gear output 66 of the gear 21, which body thereby rotates with the shaft journal 73 around its axis 67 and thus executes eccentric movements with a first and a second eccentric segment 70, 71 (FIG. 7). The eccentric body 60 has a radial, coil shaped, circumferential groove 61, both ends of which are closed, which ends form a first and second stop 68, 69 (FIG. 7). A casing 62 with radial play is placed on the eccentric body 60. A guide pin 72 (FIGS. 9, 11) pressed into the casing 62 projects with clearance into the helical groove 61 of the eccentric body 60, so that the casing 62 can only move along the coil shaped groove 61 between the front and back ends relative to the eccentric body 60.

The helical groove 61 can also lie in the casing 62 and the guide pin 72 can be arranged in the eccentric body 60. Two or more guide pins 72 can be guided in correspondingly arranged helical grooves.

The casing 62 runs radially on its exterior surface with inner clearance in an oval valve 63. Said valve is axially clamped between a disc 65 on the casing 62 and a bearing collar 64 of the casing 62, said collar running parallel to said disc. Externally, the valve 63 is guided parallel on its pair of surfaces and therefore cannot rotate simultaneously, but can execute stroke movements X-Y (FIG. 8) and an axial linear motion F-E (FIG. 10), G-H (FIG. 12), J-I (FIG. 13) with the output shafts 15, 17.

If the first electric motor 10 is driven in direction of rotation R1 (FIG. 9), then the eccentric body 60 also rotates accordingly and travels, in the case of a clockwise helical groove 61 of the casing 62 with the oval valve 63, because of the sufficiently high frictional torque between the casing 62 and the oval valve 63, so far to the front until the guide pin 72 reaches the front end (first stop 68) of the coil shaped groove 61. At this first stop 68, the eccentric body 60 rotationally engages the casing 62 and transmits the additional eccentric movement transversely to the oval on the oval valve 63 in the form of linearized stroke movements X-Y, while the movement component in the direction of the oval is offset.

The first and second output shafts 17, 18 are arranged on the oval valve 63, which shafts transmit the stroke movements X-Y of the oval valve 63 into output movements A-B or C-D. In the front stroke level of the valve 63, only the first output shaft 17 can transmit the output movements A-B to the first actuating lever 19, because the slot contour of the first driving fork 56 is somewhat broader than the diameter of the output shaft 17. The second actuating lever 20 (FIGS. 9, 12) has in the front stroke level such a broad slot contour for the second driving fork 57 that throughout the entire stroke no movement (FIG. 9) is transmitted to this actuating lever 20.

If the first electric motor 10 is now driven in the opposite direction of rotation R2 (FIG. 11), then the eccentric body 60 also rotates correspondingly. Because of the braking frictional torque between the frictional partners, the casing 62 with the valve 63 therefore travels towards the rear until the guide pin 72 reaches the rear end (second stop 69) of the coil shaped groove 61. At this second stop 69, the eccentric body 60 rotationally engages the casing 62 and transmits in the rear area the stroke movements X-Y to the valve 63, which now only activates the second actuating lever 20 according to FIG. 11.

Figures 11, 12, 13:
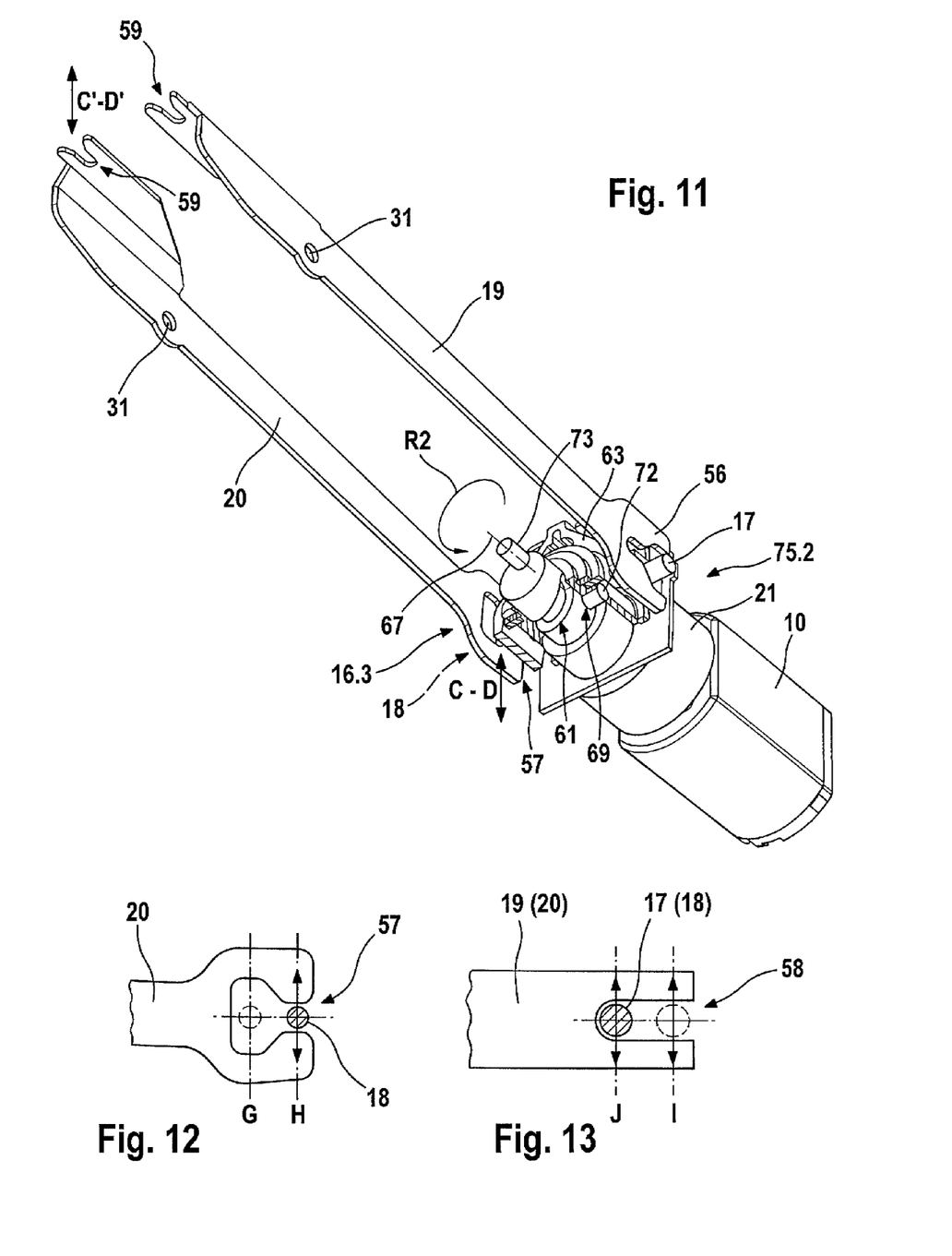
FIG. 11 shows a perspective side view of the device with the drive unit for two pumps according to FIG. 9, however, in a position "H", wherein a casing and a valve are not shown.
FIG. 12 shows a detailed representation of the second driving fork according to FIG. 11.
FIG. 13 shows a detailed representation of a third driving fork for a continuous engagement of an actuating lever.

Due to the double overrunning clutch 75 as a reversing gearbox for the device 16.3—at the end of the switching operation—in the direction of rotation R1 of the eccentric body 60, only the first actuating lever 19 is driven, which moves up and down around its swivel joint 31 and drives the first diaphragm valve pump 39 at its other end. If the eccentric body 60 is rotated in another direction R2, then after the axial switch only the second actuating lever 20 is engaged, which rotates around its swivel joint 31 and activates the second diaphragm valve pump 48.

FIG. 7 shows in a perspective side view the separately represented eccentric body 60 with a helical groove 61, which has a first and a second stop 66, 67 for the guide pin 72 (FIGS. 9, 11).

Figure 8:
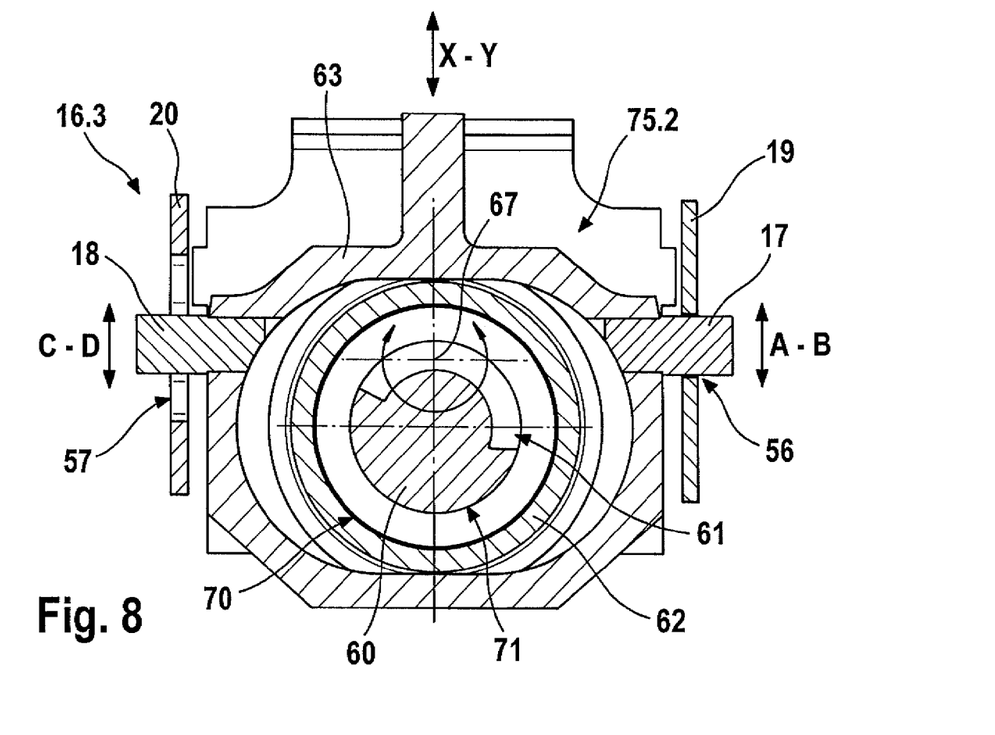
FIG. 8 shows the device from FIG. 5 in a cross section front view according to axis X-X.

FIG. 8 shows the device 16.3 in a cross section front view according to axis VII-VII of FIG. 5. Further description in more detail results from the description of FIGS. 6 and 7.

FIG. 9 shows in a perspective side view the device 16.3 with the first drive unit 9 for alternatively a first or a second pump 7, 14 (FIG. 3) corresponding to FIG. 5; however, both output shafts 15, 16 are in a position F (FIG. 10) or G (FIG. 12). By this means only the first actuating lever 19 and thus the first pump 7, 39 are driven via output movements A-B of the first output shaft 17 by output movements A'-B'. The casing 62 and the oval valve 63 are shown as a cross section.

FIG. 10 shows in a detail drawing the first driving fork 56, wherein the first actuating lever 19 is not driven in position E, but is only driven only in position F by output movements A-B.

FIG. 11 shows FIG. 9, however, both output shafts 17, 18 are in position E (FIG. 10) or H (FIG. 12), whereby only the second actuating lever 20 and thus the second pump 14, 48 are driven via output movements C-D by output movements C'-D'.

FIG. 12 shows in a detailed representation the second driving fork 57 according to FIG. 11. In position H, the second actuating lever 20 is moved by the second output shaft 18, however, said lever is not moved in position G.

FIG. 13 shows in a detailed representation a third driving fork 58 for constant activation (engagement) of the actuating levers 19, 20 independent of the position I, J of the output shafts 17, 18 and independent of the directions of rotation R1, R2. By means of this narrow configuration of the driving fork 58, a corresponding pump 7, 14 is continuously activated.

Figure 15:
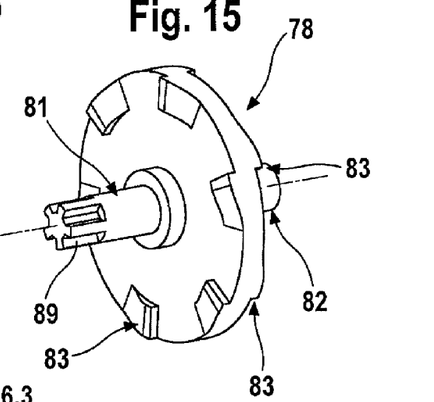
Figure 16:
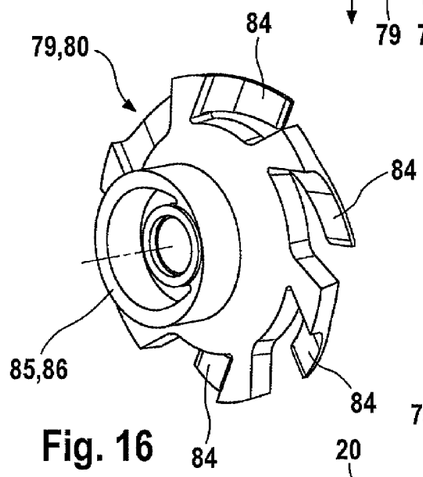
Figure 17:
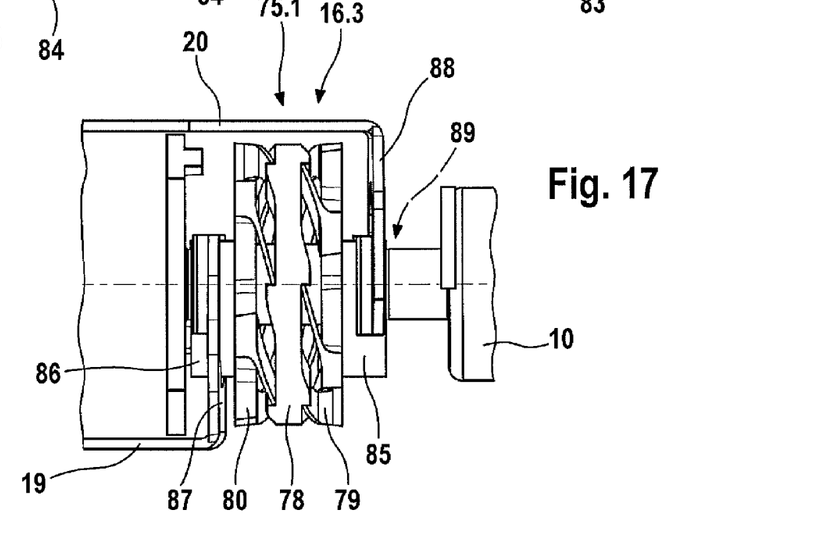
Figure 18:
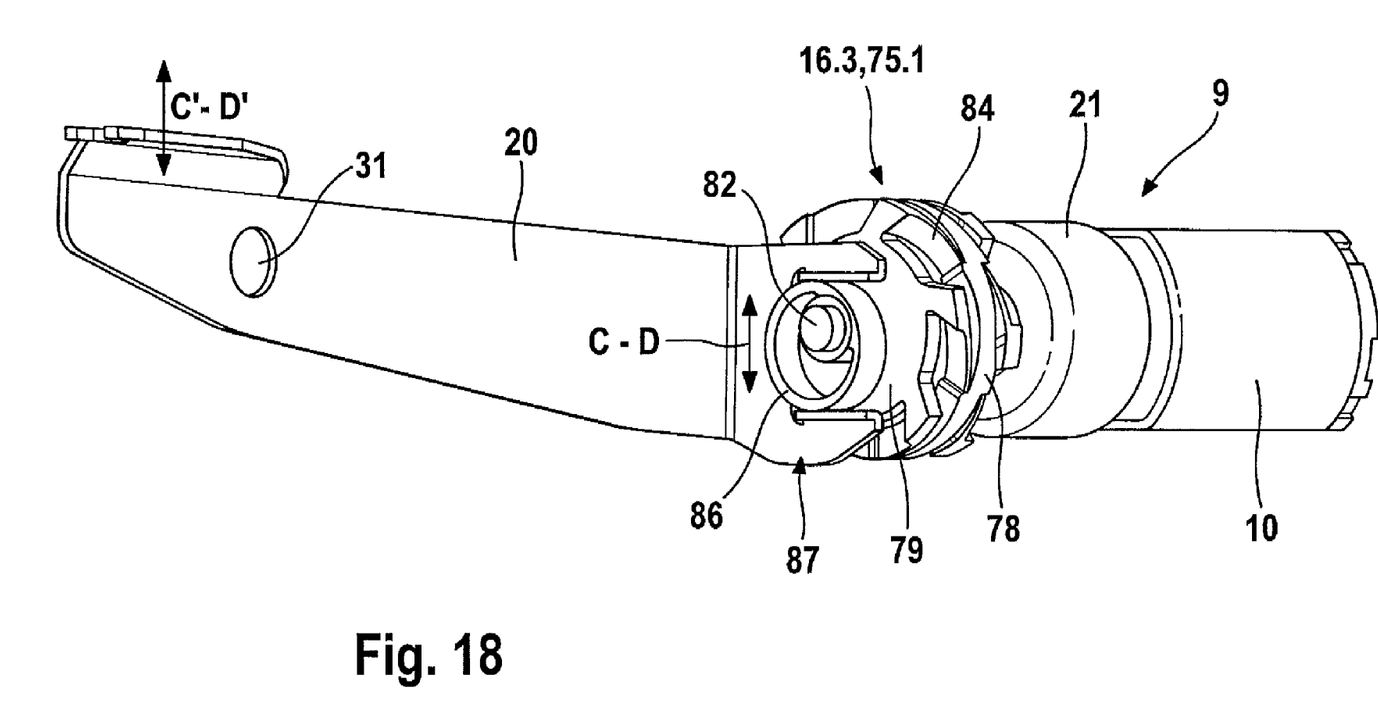

FIG. 14 through 18 show a fourth exemplary embodiment of a device 16.3 with a double overrunning clutch 75 for two opposing directions of rotation R1, R2, by means of which clutch it can alternatively switch to a first output 76 with output movements A-B or to a second output 77 with output movements C-D—in each case according to the direction of rotation R1, R2 of the first electric motor 10. The output movements A-B or C-D are generated by a first or second eccentric disc 85, 86 with a fourth and fifth driving fork 87, 88 (FIGS. 17, 18). The double overrunning clutch 75 comprises essentially three components, namely a drive wheel 78 (FIG. 15) and two identical output gears 79, 80 (FIG. 16), which working in opposite directions on a first and second shaft segment 81, 82, interact with the drive wheel 78. The shaft segment 82 is rotatable and mounted in a fixed position in the first drive unit 9. The first shaft segment 81 is provided with a coupling part 89 to connect the drive wheel 78 with the first electric motor 10 or the gear 21.

Figure 14:
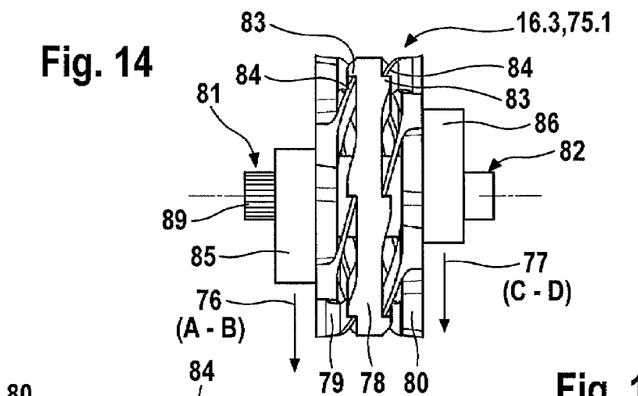
FIG. 14 through FIG. 18 show various views of a double overrunning clutch in the form of a snap fit coupling.

The drive wheel 78 has corresponding latching elements 83 which are integrally molded in one piece. The output gears 79, 80 are provided with spring elements 84 made of one piece. By this means—depending on the direction of rotation of the drive wheel 78—one of the output gears 79, 80 is engaged by the latching elements 83.

FIG. 15 shows in a perspective representation the drive wheel 78 as an individual component.

FIG. 16 shows in a perspective representation an output gear 79, 80 as an individual component.

FIG. 17 shows in a cut out the device 16.3 in interaction with the first electric motor 10 or the gear 21 and with the first and second actuating levers 19, 20.

FIG. 18 shows in a perspective representation the first drive unit 9 with the first electric motor 10 and the gear 21 of the device 16.3 and with the second actuating lever 20, wherein the first actuating lever 19 was left out for the purpose of better viewing.

The five exemplary embodiments of a device 16.1, 16.2, 16.3 shown in the figures are only to be considered by way of examples, because according to the invention all devices can be used, which depending on the direction of rotation of the first electric motor 10 alternatively can activate the first or the second pump 7, 14 of the electric toothbrush 1.

The following advantages among others result from a production/use of the electric toothbrush 1:

Compact housing 24 or hand piece.
Economization of an additional electric motor including gears for a second reservoir 13.
Ease of control of the pumps 7, 14 by means of an electric switch.
Both reservoirs 6, 13 can be easily changed.
Pumps 7, 14 can be easily changed.
Optimal concentration of the active ingredients of the dental care agents 5, 12 by correspondingly different volume flow rate profiles.
Automatic conveying of the dental care agents 5, 12, therefore safe and comfortable use.
Highest reliability of the conveying system through valves at the coupling points, which prevent drying out/clogging of the dental care agents 5, 12.

LIST OF REFERENCES

1 Electric toothbrush
2 brush head
3 Second drive unit
4 Second electric motor
5 First liquid dental care agent
6 First reservoir
7 First pump
8 First channel
9 Drive unit
10 Electric motor
11 Disposable/rechargeable battery
12 Liquid dental care agent
13 Second reservoir
14 Second pump
15 Second channel
16.1 Device
16.2 Device
16.3 Device
17 First output shaft
18 Second output shaft
19.1 Actuating lever
19.2 Actuating lever
19 First actuating lever
20 Second actuating lever
21 Gear
22 Partition
23 Soft membrane
24 Housing
25 First chamber
26 Second chamber
27 Cover
28 Brush attachment
29 Actuating zone/pump 39
30 Actuating zone/pump 48
31 Joint
32 Plastic element
33 First inlet
34 Coupling piece
35 Second inlet
36 First container neck
37 Second container neck
38 First opening
39 First diaphragm valve pump
40 Second opening
41 Control device
42 Electronic circuit board
43 Interior side
44 Flexible housing wall zone
45 Further flexible housing wall zone
46 First shaft journal
46.1 Extension/first shaft journal 46
47 Second shaft journal
48 Second diaphragm valve pump
49 Component
50 Brush head gear
56 Driving fork 57 Driving fork
58 Driving fork
59 Connecting element
60 Eccentric body
61 Helical groove
62 Casing
63 Oval valve
64 Bearing collar
65 Disc
66 Drive output
67 Axis
68 First stop
69 Second stop
70 First eccentric segment
71 Second eccentric segment
72 Guide pin
73 Shaft journal
74 Locking ring
75 Double overrunning clutch
75.0 Simple overrunning clutch
75.1 Snap fit coupling
75.2 Eccentric coupling
76 First output
77 Second output
78 Drive wheel
79 Drive wheel
80 Drive wheel
81 First shaft segment
82 Second shaft segment
83 Latching element
84 Spring element
85 First eccentric disc
86 Second eccentric disc
87 First driving fork
88 Second driving fork
89 Coupling piece
A-B Output movements
A'-B' Output movements
C'-D' Output movements
C-D Output movements
E Neutral position
F Engaged position
G Neutral position
H Engaged position
I.J Engaged position
R1 First direction of rotation
R2 Second direction of rotation
X-Y Stroke movements

What is claimed is:

1. An electric toothbrush, comprising two elements to be driven, wherein the first element is a movable brush head and the second element is a pump;
   an electric motor; and
   a device connected to the electric motor that drives the movable brush head in both directions of rotation of the electric motor and drives the pump in only one direction of rotation.

2. The electric toothbrush according to claim 1, wherein the electric motor drives the brush head with a first shaft journal and drives the pump with a second shaft journal by means of the device.

3. The small electrical appliance electric toothbrush according to claim 2, wherein the device has a simple overrunning clutch.

4. The electric toothbrush according to claim 1, including at least one reservoir for a care substance, which reservoir is connected via a pump to a channel which discharges into the brush head.

5. The electric toothbrush according claim 1, wherein the electric motor is connected to a programmable control device.

6. An electric toothbrush, comprising:
   two elements to be driven, wherein the first element is a first pump and the second element is a second pump;
   an electric motor; and
   a device connected to the electric motor that drives only the first pump in one direction of rotation of the electric motor and drives only the second pump or the first and the second pumps at the opposite direction of rotation of the electric motor.

7. The electric toothbrush according to claim 6, wherein the device has a double overrunning clutch.

8. The electric toothbrush according to claim 7, wherein the double overrunning clutch has a snap fit coupling or an eccentric coupling.

9. The electric toothbrush according to claim 8, wherein the eccentric coupling of the device has a helical groove which corresponds with a guide pin.

10. The electric toothbrush according to claim 8, wherein the snap fit coupling of the device has a centrally arranged drive wheel and on both sides of said wheel a first or second output gear, wherein latching elements on both sides of the centrally arranged drive wheel corresponds with appropriate one-sided spring elements of the first and second output gears.

* * * * *